US010988815B2

(12) United States Patent
Chen et al.

(10) Patent No.: US 10,988,815 B2
(45) Date of Patent: Apr. 27, 2021

(54) DETECTIVE MOLECULE, KIT AND METHOD FOR PREDICTING FRAGRANCE PRODUCTION IN AN ORCHID

(71) Applicant: NATIONAL CHENG KUNG UNIVERSITY, Tainan (TW)

(72) Inventors: Hong-Hwa Chen, Tainan (TW); Yu-Chen Chuang, Tainan (TW); Wen-Chieh Tsai, Tainan (TW); Yi-Chu Hung, Tainan (TW); Wen-Huei Chen, Tainan (TW); Chi-Yu Hsu, Tainan (TW); Chuan-Ming Yeh, Tainan (TW); Nobutaka Mitsuda, Ibaraki (JP); Masaru Ohme-Takagi, Ibaraki (JP)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 51 days.

(21) Appl. No.: 16/222,373

(22) Filed: Dec. 17, 2018

(65) Prior Publication Data
US 2020/0190605 A1    Jun. 18, 2020

(51) Int. Cl.
*C12Q 1/6895* (2018.01)
(52) U.S. Cl.
CPC ....... *C12Q 1/6895* (2013.01); *C12Q 2600/13* (2013.01); *C12Q 2600/148* (2013.01)
(58) Field of Classification Search
None
See application file for complete search history.

(56) References Cited

U.S. PATENT DOCUMENTS

2014/0017683 A1 *   1/2014   Yin .................... C12Q 1/6851
                                                      435/6.11

OTHER PUBLICATIONS

Chuang et al Frontiers in Plant Science. Jun. 5, 2018. vol. 9, Article 765, and Supplementary Materials, 22 pages (Year: 2018).*
Garibyan et al J Invest Dermatology. Mar. 2013. 133(3): e6, p. 1-8 (Year: 2013).*
Qiyu, X. The Degree Thesis of Department of Life Sciences, Cheng Kung University. "Exploring the relationship between difference of the repeat sequence of the GDPS promoter of Phalaenopsis and the production of fragrance", dated 2011, (Year: 2011).*
Yizhu H. Development of molecular markers from the GDPS promoter sequence for flora terpenoid scent in Phalaenopsis orchids. Jan. 22, 2016; available via URL <researchoutput.ncku.edu.tw/en/studentTheses/development-of-molecular-markers-from-the-gdps-promoter-sequence>. . . (Year: 2016).*
List of publications of Chen, Hong-Hwa, available via URL:<bio.ncku.edu.tw/english/faculty/prof-chen-hong-hwa>, printed on Aug. 5, 2020, p. 1-11. (Year: 2929).*
Office Action dated Jul. 1, 2020 issued by Taiwan Intellectual Property Office for counterpart application No. 107145433.
Search Report dated Jul. 1, 2020 issued by Taiwan Intellectual Property Office for counterpart application No. 107145433.
English Abstract Translation of Search Report issued by Taiwan Intellectual Property Office for counterpart application No. 107145433, search report dated Jul. 1, 2020.
Chuang, Yu-Chen et al., PbbHLH4 regulates floral monoterpene biosynthesis in Phalaenopsis orchids, Journal of experimental botany, 69(18), 4363-4377, Jul. 2018.
Office Action dated Jul. 24, 2020 issued by Taiwan Intellectual Property Office for counterpart application No. 107145432.
Search Report dated Jul. 24, 2020 issued by Taiwan Intellectual Property Office for counterpart application No. 107145432.
English Abstract Translation of Search Report issued by Taiwan Intellectual Property Office for counterpart application No. 107145432, search report dated Jul. 24, 2020.
Chuang, Yu-Chen et al., A Dual Repeat Cis-element Determines Express of Geranyl Diphosphate Synthase for Monoterpene Production in Phalaenopsis Orchids, Frontiers in Plant Science. Jun. 2018 vol. 9 Article 765.
Screenshot of Cheng-Kung University Library indicating a "closed shelf" status for the master's thesis of Hong Yizhu entitled Development of Molecular Markers from the GDPS Promoter Sequence for Floral Terpenoid Scent in Phalaenopsis Orchids, dated Sep. 26, 2020.
Master Thesis of Xu Qiyu at the National Cheng Kung University Department of Life Sciences entitled Analysis of the concomitance between repeats within GDPS promoter and scent production in Phalaenopsis orchids; unknown whether the thesis was ever publicly available, dated Jul. 2011.
Presentation entitled Development of molecular markers for floral scent from the GDPS promoter sequence in Phalaenopsis orchids, authored by Yi-Chu Hung, Yu-Chen Chuang, and Hong-Hwa Chen; document dated 2014 but it is unknown whether it was considered publicly available.

* cited by examiner

*Primary Examiner* — Carla J Myers
(74) *Attorney, Agent, or Firm* — WPAT, P.C., Intellectual Property Attorneys; Anthony King

(57) ABSTRACT

The invention relates to a detective molecule, and more particularly to a detective molecule and a kit for detecting a target molecule, a method for predicting fragrance production in an orchid, and a method for breeding a scented orchid.

9 Claims, 5 Drawing Sheets

Specification includes a Sequence Listing.

FIG. 2

DETECTIVE MOLECULE, KIT AND METHOD FOR PREDICTING FRAGRANCE PRODUCTION IN AN ORCHID

BACKGROUND OF THE INVENTION

1. Field of the Invention

The invention relates to a detective molecule, and more particularly to a detective molecule and a kit for detecting a target molecule, a method for predicting fragrance production in an orchid, and a method for breeding a scented orchid.

2. Description of the Related Art

*Phalaenopsis* species are widespread in the tropical Asia regions and includes approximately 56 native species (Christenson, 2001, *Phalaenopsis*: A Monograph. Portland, Oreg.: Timber Press.). Numerous *Phalaenopsis* cultivars with diverse floral appearance are obtained via breeding and have become popular orchids due to their outstanding floral display and longevity (Hsiao et al., 2011, Plant Cell Physiol. 52, 1467-1486.). In addition, some of the *Phalaenopsis* cultivars with pleasant fragrance improve their ornamental value in the floriculture market. However, breeding scented orchid cultivars under traditional breeding is difficult compared to other favorable traits (Yeh et al., 2014, Agric. Policy Agric. Situation 267, 97). The bottlenecks include long generation time (Hsiao et al., 2011, Plant Cell Physiol. 52, 1467-1486), cross incompatibility due to the differences in genome size and chromosome size among species (Hsiao et al., 2011, Plant Cell Physiol. 52, 1467-1486; Hsiao et al., 2011, *Orchid Biotechnology II*, eds W. H. Chen and H. H. Chen (Singapore: World Scientific), 145-180; Yeh et al., 2014, Agric. Policy Agric. Situation 267, 97.), and negative correlation between floral scent and other favorable traits (Hsiao et al., 2011, *Orchid Biotechnology II*, eds W. H. Chen and H. H. Chen (Singapore: World Scientific), 145-180), which is also occurred in other modern floriculture varieties (Vainstein et al., 2001, Plant Physiol. 127, 1383-1389; Dudareva and Negre, 2005, Curr. Opin. Plant Biol. 8, 113-118). In such circumstances, alternative approaches to facilitate scented orchid breeding are needed.

The majorities of *Phalaenopsis* orchids are scentless but some do emit scent volatile organic compounds (VOCs) (Kaiser, 1993, *The Scent of Orchids: Olfactory and Chemical Investigations*. Amsterdam: Elsevier). These scented species have been extensively used as breeding parents for production of scent cultivars, such as *P. amboinensis*, *P. bellina*, *P. javanica*, *P. lueddemanniana*, *P. schilleriana*, *P. stuartiana*, *P. venosa*, and *P. violace* (Hsiao et al., 2011b, Orchid Biotechnology II, eds W. H. Chen and H. H. Chen (Singapore: World Scientific), 145-180; Yeh et al., 2014, Agric. Policy Agric. Situation 267, 97). Both *P. bellina* and *P. violacea* are two very close species popular in breeding scented phenotype and emits similar but distinct floral VOCs. *P. bellina* emits mainly monoterpenoids, including citronellol, geraniol, linalool, myrcene, nerol, and ocimene (Hsiao et al., 2006, BMC Plant Biol. 6:14; 2011, *Orchid Biotechnology II*, eds W. H. Chen and H. H. Chen (Singapore: World Scientific), 145-180), while *P. violacea* emits monoterpenoids accompanied with a phenylpropanoid, cinnamyl alcohol (Kaiser, 1993, *The Scent of Orchids: Olfactory and Chemical Investigations*. Amsterdam: Elsevier). The VOCs of *P. schilleriana* contain monoterpenoids as well, including citronellol, nerol and neryl acetate (Awano et al., 1997, Flay. Frag. J. 12, 341-344).

Monoterpenoids, the most abundant constituent in volatile terpenoids (Knudsen and Gershenzon, 2006, *Biology of Floral Scent*, eds N. Dudareva, and E. Pichersky (Boca Raton, Fla.: CRC Press), 27-52; Nagegowda et al., 2010, *The Chloroplast: Basics and Application*, eds C. A. Rebeiz, C. Benning, H. J. Bohnert, H. Daniell, J. K. Hoober, H. K. Lichtenthaler et al. (Dordrecht: Springer), 139-154), are involved in specialized interactions with other organisms and surrounding environment (Tholl, 2015, Biotechnology of Isoprenoids, eds J. Schrader, and J. Bohlmann (Cham: Springer), 63-106). Apart from their roles in nature, monoterpenoids are widely used in flavor, cosmetics, and perfumery industries due to their unique and pleasant fragrance characteristics (Schwab et al., 2008, Plant J. 54, 712-732).

The precursors of monoterpenoids, IDP and its isomer, DMADP, are produced from the methylerythritol phosphate (MEP) pathway in the plastid. The short-chain prenyltransferases, GDPS, is responsible for the head-to-tail condensation of IDP and DMADP to generate the direct substrate GDP for monoterpene synthases (Dudareva et al., 2004, Plant Physiol. 135, 1893-1902). In *Phalaenopsis* orchids, PbGDPS is characterized as the key enzyme to provide precursors for monoterpene biosynthesis in *P. bellina* (Hsiao et al., 2008, Plant J. 55, 719-733). Interestingly, recombinant PbGDPS possesses dual prenyltransferase activities for the production of both GDP and farnesyl diphosphate (FDP), the precursor for monoterpeneoids, and sesquiterpenoids, respectively (Hsiao et al., 2008, Plant J. 55, 719-733). Expression of PbGDPS is concomitant with the emission of monoterpenoids during flower developments, peaked on day 5 post anthesis (D+5) (Hsiao et al., 2008, Plant J. 55, 719-733). Accordingly, it is necessary to investigate the promoter of the GDPS gene which affects the expression thereof.

SUMMARY OF THE INVENTION

The present invention provides a detective molecule, a kit and a method for predicting fragrance production in an orchid.

One subject of the invention is to provide a detective molecule for detecting a target molecule, which target molecule is selected from the group consisting of:
  (i) a nucleic acid molecule having a nucleotide sequence of SEQ ID NO: 1;
  (ii) a nucleic acid molecule having a nucleotide sequence of SEQ ID NO: 2; and
  (iii) a nucleic acid molecule having a nucleotide sequence of at least 95% similarity to the nucleic acid molecule defined in (i) or (ii).

Another subject of the invention is to provide a kit for detecting a target molecule, comprising the detective molecule mentioned above.

Still another subject of the invention is to provide a method for predicting fragrance production in an orchid, comprising detecting if a target molecule exists in genome of the orchid, wherein the target molecule is selected from the group consisting of:
  (i) a nucleic acid molecule having a nucleotide sequence of SEQ ID NO: 1;
  (ii) a nucleic acid molecule having a nucleotide sequence of SEQ ID NO: 2; and (iii) a nucleic acid molecule having a nucleotide sequence of at least 95% similarity to the nucleic acid molecule defined in (i) or (ii).

Still another subject of the invention is to provide a method for breeding a scented orchid, comprising predicting fragrance production in an orchid by the method mentioned above.

BRIEF DESCRIPTION OF THE DRAWINGS

FIG. 2: The sequence alignment of PbGDPSp, PaGDPSpA and PaGDPSpB. The two units of the dual repeat are labeled with the thick color bars above the alignment. The subunits of R1 and R2 are labeled with the color lines under the alignment. The sequence alignment was generated by using Clustal Omega and displayed by using BOXSHADE.

DETAILED DESCRIPTION OF THE INVENTION

Figure 1:
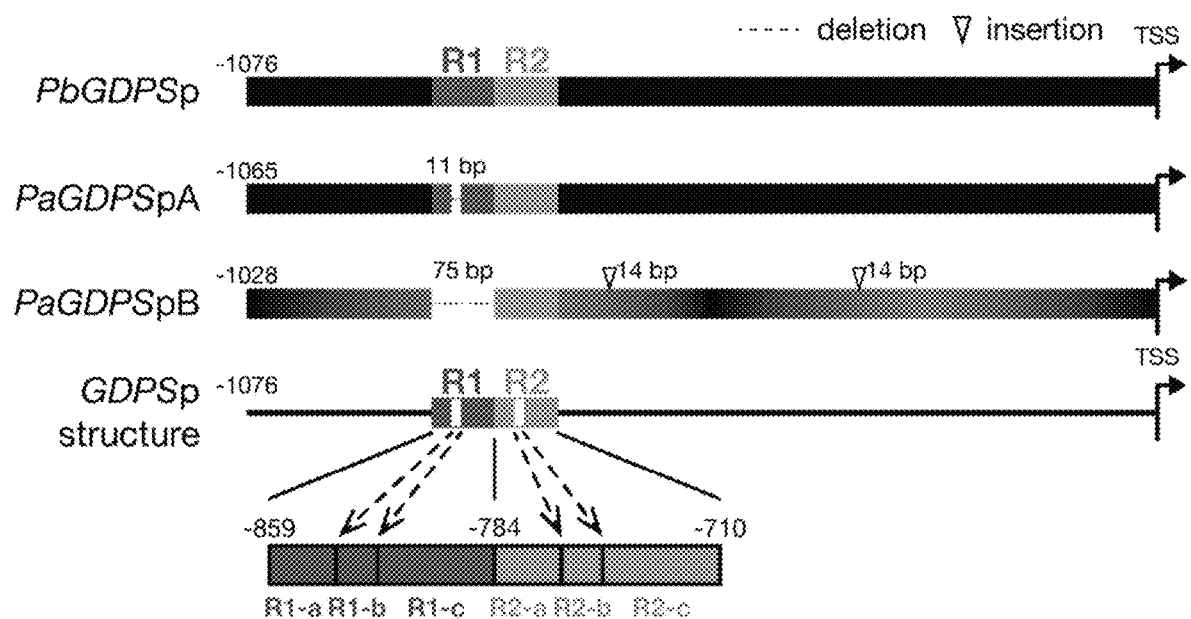
FIG. 1: Promoter structure of GDPS. Promoter structure of GDPS was revealed by the comparison of three sequences of PbGDPSp, PaGDPSpA, and PaGDPSpB. Two repeats located from −859 bp to −710 bp of PbGDPSp were named as R1 and R2. The repeat was further dissected into three subunits based on 11-bp deletion located in the center of R1. This deletion was referred as R1-b, and the sequences prior to and behind R1-b was R1-a and R1-c, respectively. The corresponding dissection in R2 was R2-a, R2-b, and R2-c. TSS indicates the translation start site (ATG). Black color gradient in PaGDPSpB indicated its numerous substitutions compared to PbGDPSp.

One subject of the invention is to provide a detective molecule for detecting a target molecule, which target molecule is selected from the group consisting of:
(i) a nucleic acid molecule having a nucleotide sequence of SEQ ID NO: 1;
(ii) a nucleic acid molecule having a nucleotide sequence of SEQ ID NO: 2; and
(iii) a nucleic acid molecule having a nucleotide sequence of at least 95% similarity to the nucleic acid molecule defined in (i) or (ii).

As utilized in accordance with the present disclosure, the following terms, unless otherwise indicated, shall be understood to have the following meanings:

The term "polynucleotide" as referred to herein means single-stranded or double-stranded nucleic acid polymers of at least 10 bases in length. In certain embodiments, the nucleotides comprising the polynucleotide can be ribonucleotides or deoxyribonucleotides or a modified form of either type of nucleotide. Said modifications include base modifications such as bromuridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

In one preferred embodiment of the invention, the target molecule of (i) is a nucleic acid molecule having a nucleotide sequence of SEQ ID NO: 1, which is a 150-bp polynucleotide derived from −859 to −710 of a promoter of geranyl diphosphate synthase (GDPS) gene of *Phalaenopsis bellina* (Orchidaceae).

The target molecule in (i) is a dual repeat cis-element, i.e., includes two 75-bp units with a same nucleotide sequence (i.e., SEQ ID NO: 2). The first and second 75-bp units are denoted as 'R1', and a2', respectively. The R1 and R2 units are in a same direction.

Hence, in another preferred embodiment of the invention, the target molecule of (ii) is a nucleic acid molecule having a nucleotide sequence of SEQ ID NO: 2, which is a 75-bp polynucleotide derived from −859 to −785 of the promoter of the GDPS gene (i.e., R1 unit), or derived from −784 to −710 of the promoter of the GDPS gene (i.e., R2 unit).

While not willing to be bound by any theory, it is believed that the R1 and/or R2 unit is crucial for GDPS promoter activity in an orchid. For example, a GDPS promoter containing both R1 and R2 units shows approximately three folds increase as compared to a GDPS promoter containing only R2 units, and approximately five folds increase as compared to a GDPS promoter without R1 and R2 units.

In one preferred embodiment of the invention, the target molecule of (iii) is a nucleic acid molecule having a nucleotide sequence of at least 95% similarity to the nucleic acid molecule defined in (i) or (ii). As used herein, a nucleic acid molecule having a nucleotide sequence of at least 95% similarity to a reference nucleic acid molecule (such as SEQ ID NO: 1 or 2) refers to a nucleic acid molecule that differ from the reference nucleic acid molecule by substitution, deletion or insertion. For example, one or more of a nucleic acid residue is substituted with another nucleic acid residue. The similarity between the nucleic acid molecule of (iii) to a reference nucleic acid molecule (such as SEQ ID NO: 1 or 2) may be measured by any well-known algorithm of sequence identity, such as FASTA, BLAST or Gap.

In one preferred embodiment of the invention, the target molecule of (iii) is a nucleic acid molecule having a nucleotide sequence of at least 95% or 99% similarity to the nucleic acid molecule defined in (i) or (ii). In one more preferred embodiment of the invention, the target molecule of (iii) is a nucleic acid molecule having a nucleotide sequence of at least 99% similarity to the nucleic acid molecule defined in (i) or (ii).

In one preferred embodiment of the invention, the target molecule is located in an orchid. Preferably, the orchid is a *Phalaenopsis* spp.

In one preferred embodiment of the invention, the target molecule is located in a promoter of geranyl diphosphate synthase gene, such as an upstream promoter of GDPS gene.

In one preferred embodiment of the invention, the detective molecule is a primer for specifically amplifying the target molecule. For example, the primer may be specific to a portion of the GDPS promoter outside the R1 and R2 units. Preferably, the primer is selected from a forward primer having a nucleotide sequence of SEQ ID NO: 3 (TTGCCTCGAGATTTGTTTCGGAGGATGGA) and a reverse primer having a nucleotide sequence of SEQ ID NO: 4 (ACCTAAGGATGCATGGGCCATACTAG).

In another preferred embodiment of the invention, the detective molecule may be a nucleic acid probe which can be hybridized with the target molecule.

Another subject of the invention is to provide a kit for detecting a target molecule, comprising the detective molecule mentioned above. In one preferred embodiment of the invention, the kit further comprises deoxynucleoside triphosphates, DNA polymerase and buffers.

Still another subject of the invention is to provide a method for predicting fragrance production in an orchid, comprising detecting if a target molecule exists in genome of the orchid, wherein the target molecule is selected from the group consisting of:

(i) a nucleic acid molecule having a nucleotide sequence of SEQ ID NO: 1;

(ii) a nucleic acid molecule having a nucleotide sequence of SEQ ID NO: 2; and (iii) a nucleic acid molecule having a nucleotide sequence of at least 95% similarity to the nucleic acid molecule defined in (i) or (ii).

For example, the target molecule may be detected by hybridization, PCR amplification, and/or DNA sequencing.

In one preferred embodiment of the invention, the orchid is a *Phalaenopsis* spp.

In one preferred embodiment of the invention, the method comprises detecting if the target molecule exists in a promoter of geranyl diphosphate synthase gene.

In one preferred embodiment of the invention, the method comprises detecting the target molecule using a detective molecule, such as the detective molecule mentioned above.

In one preferred embodiment of the invention, the method comprises the steps of:

(a) obtaining a nucleic acid segment from the orchid;

(b) performing an amplification with the nucleic acid segment as a template to obtain an product containing the target molecule; and (c) analyzing a product of the amplification.

The genomic DNA of the orchid may be extracted by any known methods, such as extracted by using Plant Genomic DNA Purification Kit (Bio-GPD50, Biokit, Taiwan). Then, the amplification may be achieved by polymerase chain reaction (PCR).

In one preferred embodiment, the step (b) comprises performing a polymerase chain reaction with a primer selected from a forward primer having a nucleotide sequence of SEQ ID NO: 3 and a reverse primer having a nucleotide sequence of SEQ ID NO: 4.

In one preferred embodiment, the step (c) comprises determining the length of the product of the amplification by gel electrophoresis, such as agarose gel electrophoresis.

Agarose gel electrophoresis facilitates the separation of DNA based upon size in a matrix composed of a highly purified form of agar. Nucleic acids tend to become oriented in an end on position in the presence of an electric field. Migration through the gel matrices occurs at a rate inversely proportional to the log 10 of the number of base pairs.

Alternatively, the step (c) comprises sequencing the product of the amplification.

For example, the sequencing process involves determining the positions of each of the four major nucleotide bases, adenine (A), cytosine (C), guanine (G), and thymine (T) along the DNA molecule(s) of an organism. Short sequences of DNA are usually determined by creating a nested set of DNA fragments that begin at a unique site and terminate at a plurality of positions comprised of a specific base. The fragments terminated at each of the four natural nucleic acid bases (A, T, G and C) are then separated according to molecular size in order to determine the positions of each of the four bases relative to the unique site. The pattern of fragment lengths caused by strands that terminate at a specific base is called a "sequencing ladder." The interpretation of base positions as the result of one experiment on a DNA molecule is called a "read." There are different methods of creating and separating the nested sets of terminated DNA molecules.

In an example, we compare the GDPS promoter regions of scented orchids (e.g., *P. bellina, P. lueddemanniana,* P. I-Hsin Venus, and P. Meidarland Bellina Age) with the GDPS promoters the scentless orchids (e.g., *P. amboinensis, P. schilleriana,* and *P. cornu-cervi*) in genome by amplifying with the forward primer having a nucleotide sequence of SEQ ID NO: 3 and the reverse primer having a nucleotide sequence of SEQ ID NO: 4. As shown in the result of electrophoresis (FIG. 4), schematically figure (FIG. 3B) and the monoterpenoids production (FIG. 3A), the monoterpene production is correlated to the existence of the target molecule in genome of the orchid.

Figure 5:
FIG. 5: Luciferase activities of dissected PbGDPS promoters in P. I-Hsin Venus by particle bombardment, with serial deletion of PbGDPS promoter to analyze the putative cis-element. Statistic tests were performed by using Tukey's honestly significant difference test at a=0.05.

Further, the effect of the target molecule to the expression of the structure gene is investigated. The activity of PbGp-859 (containing R1 and R2 units), PbGp-784 (R1 unit deleted) and PbGp-710 (R1 and R2 units both deleted) were evaluated in P. I-Hsin Venus flowers for dual luciferase assays. It is found that a GDPS promoter containing both R1 and R2 units shows approximately three folds increase as compared to a GDPS promoter containing only R2 units, and approximately five folds increase as compared to a GDPS promoter without R1 and R2 units (FIG. 5).

Still another subject of the invention is to provide a method for breeding a scented orchid, comprising predicting fragrance production in an orchid by the method mentioned above.

The following Examples are given for the purpose of illustration only and are not intended to limit the scope of the present invention.

EXAMPLE

Materials and Methods

Plant Material and Growth Conditions

Five native and two cultivar hybrids were used in the study, including *P. amboinensis* var. *yellow* (abbreviated as *P. amboinensis*), *P. bellina, P. cornucervi* var. *red* (abbreviated as *P. cornu-cervi*), *P. lueddemanniana, P. schilleriana,* P. I-Hsin Venus 'KHM2212' (abbreviated as P. I-Hsin Venus), and P. Meidarland Bellina Age 'LM128' (abbreviated as P. Meidarland Bellina Age). These individual plants were collected from various orchid nurseries across Taiwan (details in Table 1 below).

All the plant materials were grown in the greenhouse at National Cheng Kung University (NCKU) under natural light and surrounding temperature from 27 to 30° C. in spring and summer with 75-85% humidity.

TABLE 1

Sources of the 7 *Phalaenopsis* orchids used in this study.

| | Name (by alphabetical order) | Source (Taiwan) |
|---|---|---|
| Species | *P. amboinensis* var. yellow | Tung-Hai Orchids |
| | *P. bellina* | Ming-Hui Orchids Nursery |
| | *P. cornu-cervi* var. red | Mi-Tuo Orchids |

TABLE 1-continued

Sources of the 7 *Phalaenopsis* orchids used in this study.

| | Name (by alphabetical order) | Source (Taiwan) |
|---|---|---|
| Hybrid | P. lueddemanniana | Mi-Tuo Orchids |
| | P. schilleriana | Han-Lin Orchids |
| | P. I-Hsin Venus | I-Hsin Biotechnology Corp. |
| | P. Meidarland Bellina Age 'LM128' | Meidarland Orchids |

Gas Chromatographic Analysis of Floral Volatiles

Analysis of the floral VOCs of 7 *Phalaenopsis* orchids was carried out according to the previous studies (Hsiao et al., 2006, BMC Plant Biol. 6:14; Chuang et al., 2017, Bot. Stud. 58:50). The VOCs were collected during the most emitted scent period (from 10:00 to 16:00) by using solid phase extraction system (DSC-Si and DCS-18, Supelco, United States) as described (Chuang et al., 2017, Bot. Stud. 58:50), and the compounds were then identified by using gas chromatography/high-resolution mass spectrometry (GC/HRMS) at the NCKU Instrument Center (Hsiao et al., 2006, BMC Plant Biol. 6:14). To assess the amounts of each compound, 1 mg of ethyl myristate was recruited as the internal standard (Fluka, Honeywell, United States).

Detection of GDPS Gene Sequence, Upstream Regulatory Fragment and the Dual Repeat Region in 7 Orchid Genomes To detect the GDPS gene and its upstream regulatory fragment, the genomic DNA of 7 *Phalaenopsis* orchids were extracted by using Plant Genomic DNA Purification Kit (Bio-GPD50, Biokit, Taiwan). Standard PCRs were applied to amplify the N-terminal region of GDPS (~400-bp) with the primer designed based on PbGDPS genomic sequence (all the primers used here and thereafter were listed Table 2 below) since PbGDPS is an intronless gene (Hsiao et al., 2008, Plant J. 55, 719-733). The 1-kb upstream promoter fragments of GDPS were also isolated from the 7 *Phalaenopsis* orchids using the designed primers based on the genomic DNA of *P. bellina* (Chuang et al., 2017, Bot. Stud. 58:50). The dual repeat region was then amplified and cloned with ZeroBack Fast Ligation Kit (TIANGEN, China). Six to eight colonies were selected randomly for sequencing. The presence of the cis-elements in the dual repeats was predicted using PlantPAN (Chow et al., 2015, Nucleic Acids Res. 44, D1154-D1160), with 100% similar score accepted as the predicted results.

TABLE 2

List of oligonucleotide primers used in this study.

| Purpose | Sequence (5' to 3') | |
|---|---|---|
| Target | Forward | Reverse |
| Detection of GDPS gene, promoter and dual-repeat | | |
| Gene | ATGGCAGCAATCTTTCCC TCAATCCCCTCCAATTT (SEQ ID NO: 5) | CGAGGGGAGGGGCG GTGCG (SEQ ID NO: 6) |
| Promoter | GCCTCGAGATTTGTTTCG G (SEQ ID NO: 7) | CCATGGTTTTTTGGG TTTGAAAGGAGAG (SEQ ID NO: 8) |
| Dual repeat | TTGCCTCGAGATTTGTTT CGGAGGATGGA (SEQ ID NO: 3) | ACCTAAGGATGCATG GGCCATACTAG (SEQ ID NO: 4) |

TABLE 2-continued

List of oligonucleotide primers used in this study.

| Purpose | Sequence (5' to 3') | |
|---|---|---|
| Target | Forward | Reverse |
| Transient assay construction | | |
| PbGp-859 | GGATCCTATAGAATCCA AAATGTATAGACCCT (SEQ ID NO: 9) | CCATGGTTTTTTGGG TTTGAAAGGAGAG (SEQ ID NO: 10) |
| PbGp-784 | GGATCCGAATCCAAAAT GTATAGACCCTTG (SEQ ID NO: 11) | CCATGGTTTTTTGGG TTTGAAAGGAGAG (SEQ ID NO: 12) |
| PbGp-710 | GGATCCGCCCATGCATCC TTAGGTCTGTTAA (SEQ ID NO: 13) | CCATGGTTTTTTGGG TTTGAAAGGAGAG (SEQ ID NO: 14) |

Plasmid Construction

The serial deletion fragments of the promoter fragment upstream from the translation start site of PbGDPS (PbGp-859, PbGp-784, PbGp-710) (FIG. 5) were amplified from the genomic DNA of *P. bellina*. Specific primers with the restriction endonuclease sites of BamH I and Nco I were designed to amplify these truncated fragments. The amplified fragments were double-digested with the restriction enzyme BamH I and Nco I, and cloned into the corresponding enzyme digestion sites of pJD301(f) to drive the firefly (Photinus pyralis) luciferase gene (Hsu et al., 2014, PLoS One 9:e106033). All constructs were verified by DNA sequencing. The promoter-LUC constructs were schematically presented in FIG. 5.

Transactivation Assay of PbGDPS Promoter Fragments in Planta

The promoter-LUC constructs were bombarded into the floral tissues of P. I-Hsin Venus with an internal control plasmid, pJD301(R), containing the *Renilla* luciferase gene driven by cauliflower mosaic virus (CaMV) 35S promoter. For normalization, the luciferase activity of the reporter construct was divided by that of the internal control. The involvement of internal control reduced experimental variability resulted from differential bombardment efficiency and transformation efficiency among various experimental groups. The amount of the reporter plasmid and the internal control was 10 and 0.1 mg, respectively. At least six individual flowers of P. I-Hsin Venus were employed for replicates. Luciferase activity of each sample was measured (Hsu et al., 2014, PLoS One 9:e106033). For statistics analysis between two groups, pairwise comparisons were performed by using Tukey's honestly significant difference test at $\alpha=0.05$.

Results

Isolation of a Dual Repeat in the GDPS Upstream Promoter

Previously, two individual 1-kb fragments of GDPS promoters were isolated from the scentless *P. aphrodite*, namely PaGDPSpA and PaGDPSpB. Compared to the GDPS promoter from the scented *P. bellina* (PbGDPSp), two GDPS promoters identified from *P. aphrodite*, PaGDPSpA and PaGDPSpB contained an 11-bp deletion and a 75-bp deletion, respectively (FIG. 1). PaGDPSpB also had two 14-bp insertions in addition to numerous nucleotide substitutions. By performing the luciferase promoter assays in planta, PaGDPSpA showed the similar promoter activity as PbGDPSp either in scented or scentless flowers, while PaGDPSpB revealed very low promoter activity even in the scented *P. bellina* floral tissues. These results indicated that the lack of the 75-bp region in the PaGDPSpB is detrimental for its activity. Further sequence analysis of the PbGDPS promoter showed that a second 75-bp repeat is present downstream from the original 75-bp repeat and formed a dual repeat consisted of the two 75-bp units. The first and second 75-bp units were then denoted as 'R1', and 'R2', respectively, located from −859 to −710 nt upstream from the ATG (FIG. 1).

Figure 2:
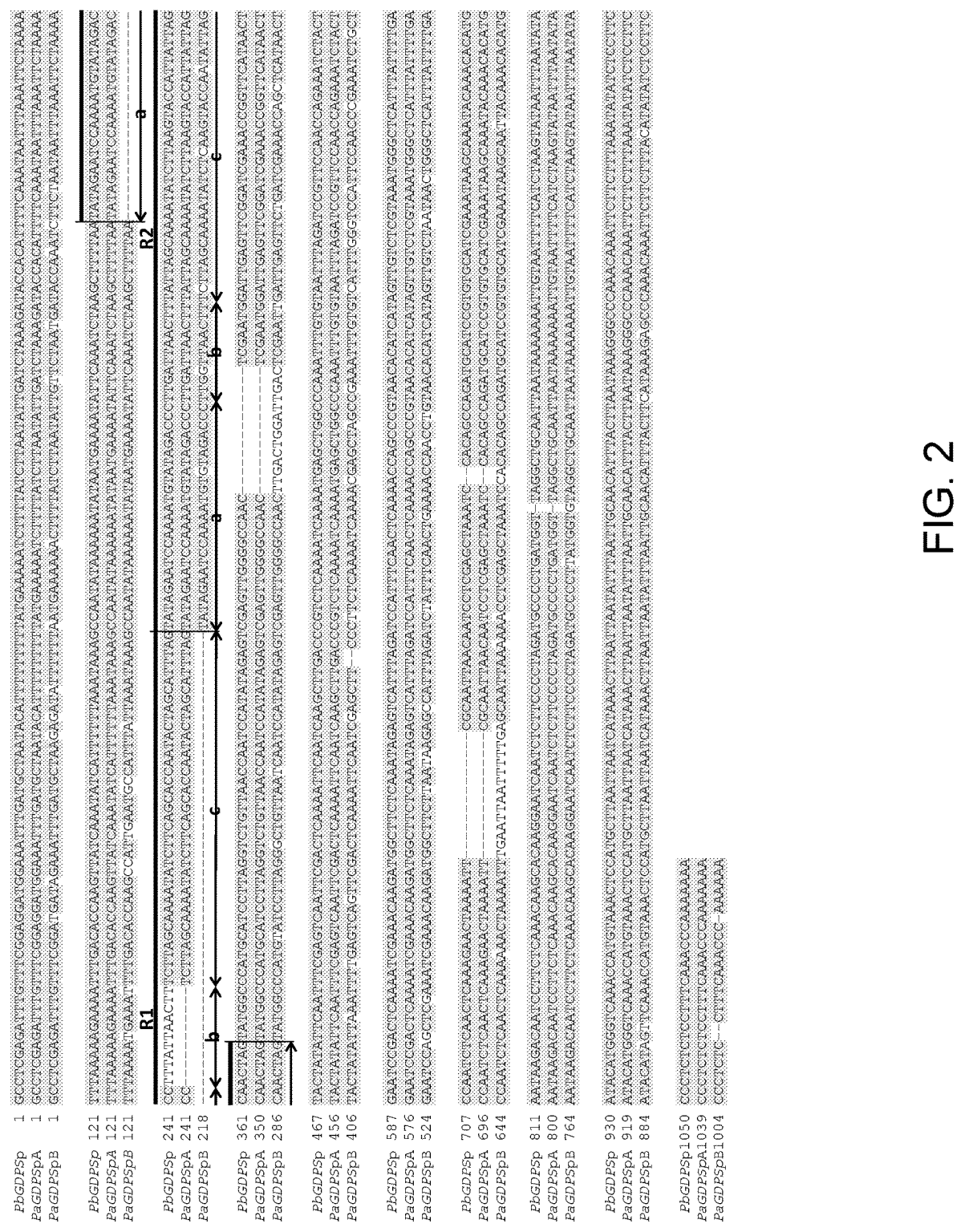

The PaGDPSpB lacked the entire R1 unit, and PaGDPSpA harbored a 11-bp deletion in the center of R1, which was defined as R1-b subunit (FIG. 1). The region (25-bp) prior to the R1-b was denoted as R1-a, and those (39-bp) behind was R1-c, and the corresponding divisions in R2 were denoted as R2-a, R2-b and R2-c (FIG. 1). The dual repeat structure was schematically represented in FIG. 1, and the sequence of the dual repeat is in FIG. 2. The difference between the GDPS promoters of the scent *P. bellina* and the scentless *P. aphrodite* resided in the dual repeat, and this is well correlated with the monoterpene phenotype.

Concomitance of the Integrity of the Dual Repeat with the Monoterpene Production According to the promoter analysis results of PaGDPS and PbGDPS from scented and scentless *Phalaenopsis* orchids, we hypothesized that the dual repeat is associated with the monoterpene production. To confirm this, 7 frequently used breeding parents of *Phalaenopsis* orchids (Table 1) were recruited and assessed for the correlation analysis between the dual repeat and the monoterpene production.

We first examined the floral scent profile and found that four orchids emitted monoterpenoids, including P. Meidarland Bellina Age, *P. bellina*, P. I-Hsin Venus, and *P. lueddemanniana*. In contrast, the major VOCs of *P. amboinensis* were sesquiterpenoids and benzenoids. *P. schilleriana* emitted trace amounts of benzenoids. *P. comucervi* was considered as "scentless" since no scent compounds were detected. For brief, the relative amounts of monoterpenoids emitted from these *Phalaenopsis* orchids were symbolized in FIG. 3A.

Figure 3:
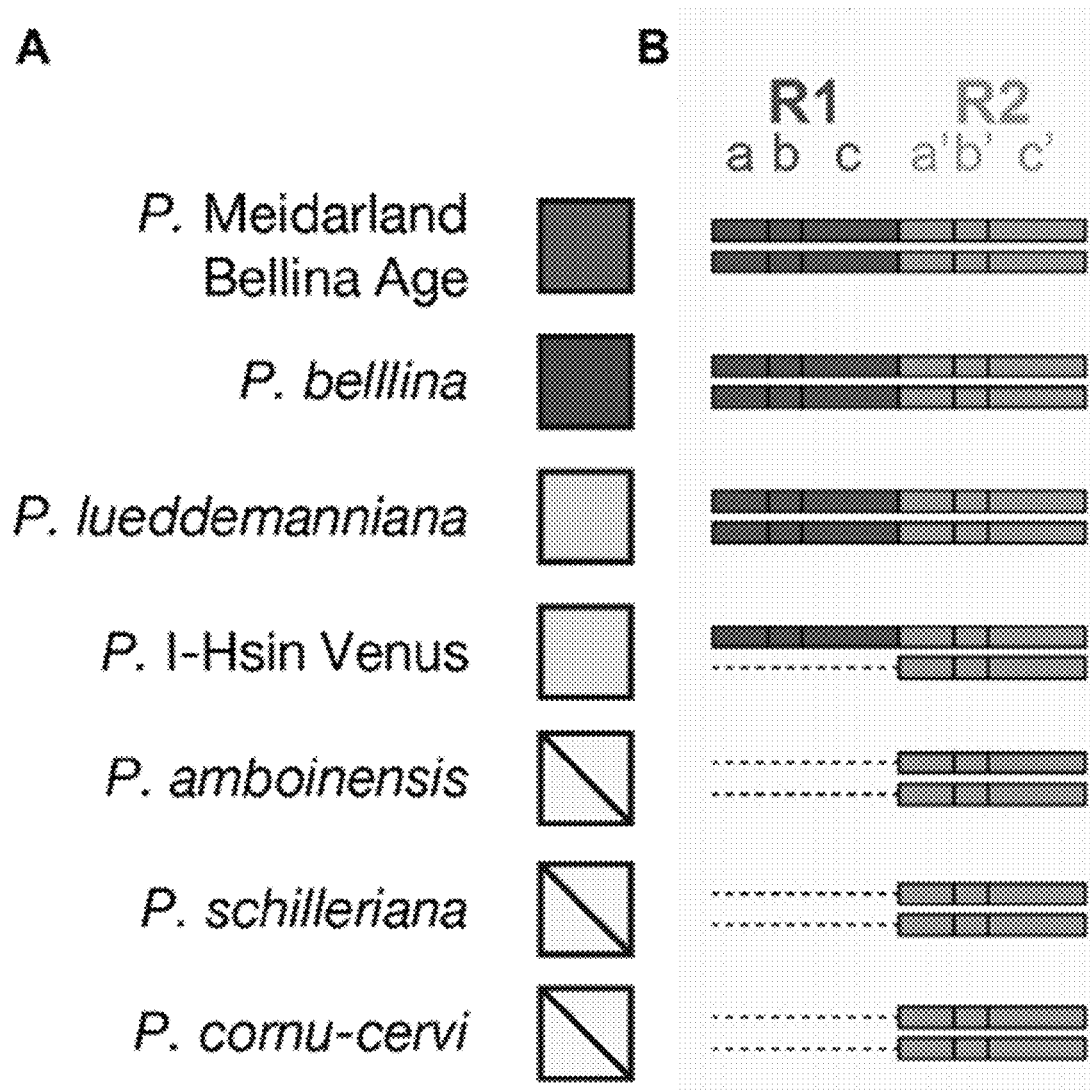
FIG. 3: The analysis of the floral volatiles and dual-repeat in 7 *Phalaenopsis* orchids. (A) The relative amounts of floral volatiles were represented by a black color gradient. The block with a diagonal line indicates that no monoterpenoid is identified in this orchid. (B) The dual repeat structure of GDPS promoter.
Figure 4:
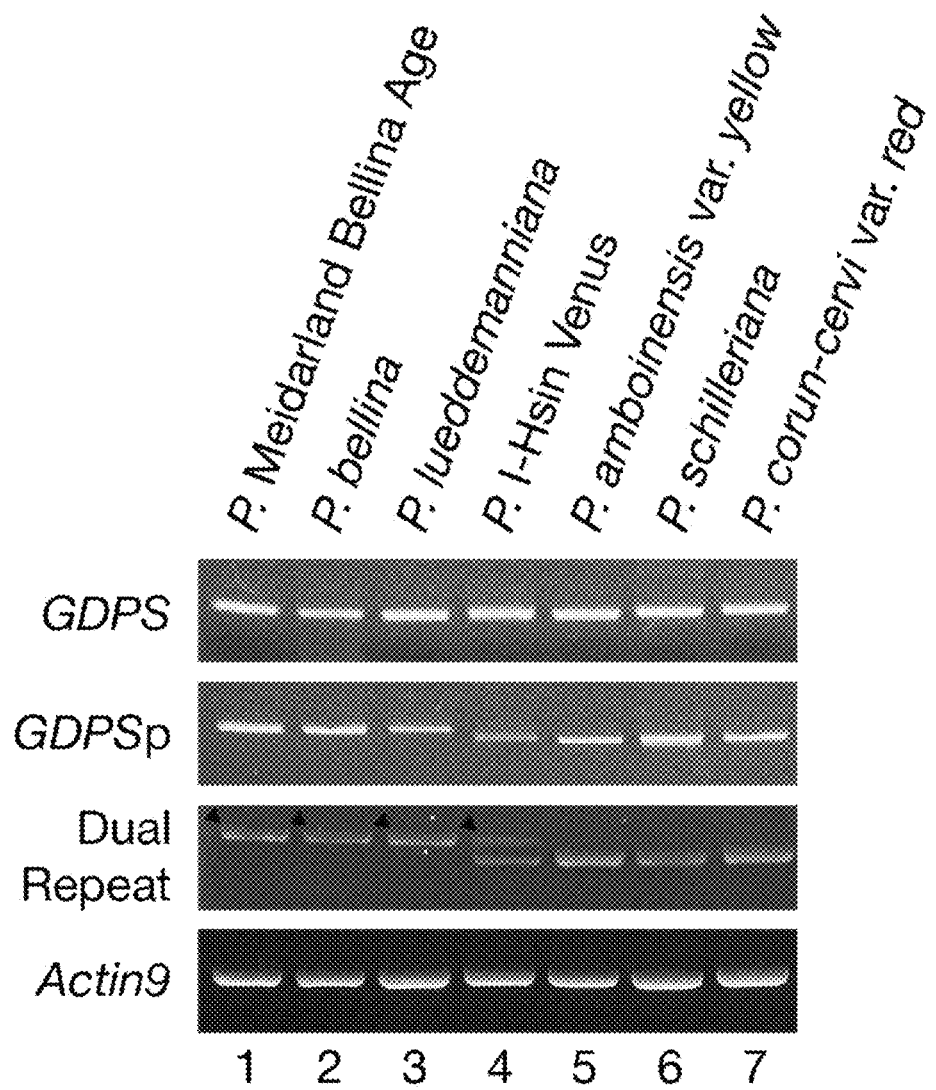
FIG. 4: PCR amplification of the GDPS gene, its 1-kb promoter fragment and the dual repeat in the genomic DNA of 7 *Phalaenopsis* orchids. Actin was used as a control. Amplification of 1-kb promoter and dual repeat showed polymorphisms.

The presence of the GDPS gene and its promoter sequence in the 7 *Phalaenopsis* orchids were then analyzed (FIG. 4). Intriguingly, the GDPS gene was present in all of these orchids regardless of being scent or scentless phenotype (FIG. 4). It is plausible that the defects are resided in the promoter region (GDPSp, FIG. 4). We then amplified the dual repeat on GDPSp and a polymorphism of the dual repeat fragment length was detected among the 7 *Phalaenopsis* orchids (FIG. 4). The four scented orchids with monoterpene production contain the complete dual repeat (FIG. 4, the black arrowheads). In contrast, the amplified dual repeat fragments of the other orchids were reduced to various extents with various deletions in the dual repeat region. These 7 fragments were cloned and sequenced. Deletions in the dual repeats were detected in the R1 unit, which appear to cause defects in GDPS promoter activities in the orchids without monoterpene production (FIG. 3A, 3B).

Taken together, we concluded that the integrity of the dual repeat in the GDPS promoter is strongly correlated with its elevated expression and thus the monoterpene production.

The Dual Repeat is Crucial for GDPS Promoter Activity

To investigate the role of the dual repeat in the promoter activity of GDPS, the ~2-kb promoter fragment (denoted PbGp-2010) upstream from the start site of PbGDPS was isolated and subjected to serial deletions. The activity of PbGp-859 (containing R1 and R2 units), PbGp-784 (R1 unit deleted) and PbGp-710 (R1 and R2 units both deleted) were evaluated in P. I-Hsin Venus flowers via particle bombardment for dual luciferase assays. It was legitimate that we should examine PbGDPS promoter activity in the original species *P. bellina*. However, the supply of *P. bellina* flowers fell short of demand for experiments as *P. bellina* commonly produces only one flower per 20 days. Instead, P. I-Hsin Venus, the offspring of *P. bellina* emitting similar scents, was micropropagated to large quantities with the identical genetic background and would help to reduce variation.

The highest luciferase activity was observed for PbGp-859, which showed approximately threefold increase as compared to that PbGp-784, and fivefold increase as compared to that of PbGp-710 (FIG. 5). Thus, the cis-element responsible for high promoter activity was between nucleotide (nt) −859 and nt −710 (150-bp), in which the dual repeat located. These results verified that the dual repeat plays a crucial role for PbGDPS promoter activity.

While embodiments of the present invention have been illustrated and described, various modifications and improvements can be made by persons skilled in the art. The present invention is not limited to the particular forms as illustrated, and that all the modifications not departing from the spirit and scope of the present invention are within the scope as defined in the appended claims.

What is claimed is:

1. A method for predicting fragrance production in an orchid, comprising detecting if a target molecule exists in genome of the orchid, wherein the target molecule is selected from the group consisting of:
   (i) a nucleic acid molecule comprising SEQ ID NO: 1;
   (ii) a nucleic acid molecule comprising SEQ ID NO: 2; and wherein the existence of the target molecule in genome of the orchid predicts fragrance production in the orchid;
      wherein the detecting comprises amplifying the target molecule using a primer;
      wherein the primer is selected from a forward primer comprising SEQ ID NO: 3 and a reverse primer comprising SEQ ID NO: 4.

2. The method according to claim 1, wherein the orchid is a *Phalaenopsis* spp.

3. The method according to claim 1, further comprising detecting if the target molecule exists in a promoter of geranyl diphosphate synthase gene.

4. The method according to claim 1, further comprising the steps of:
   (a) obtaining a nucleic acid segment from the orchid;
   (b) analyzing a product of the amplification.

5. The method according to claim 4, wherein amplifying comprises performing a polymerase chain reaction.

6. The method according to claim 4, wherein the step comprises determining the length of the product of the amplification by gel electrophoresis.

7. The method according to claim 4, wherein the step comprises sequencing the product of the amplification.

8. A method for breeding a scented orchid, comprising predicting fragrance production in an orchid by the method according to claim 1 and breeding the orchid having the target molecule.

9. The method according to claim 8, wherein the amplifying comprises performing a polymerase chain reaction.

* * * * *

SEQUENCE LISTING

<160> NUMBER OF SEQ ID NOS: 14

<210> SEQ ID NO 1
<211> LENGTH: 150
<212> TYPE: DNA
<213> ORGANISM: Phalaenopsis bellina

<400> SEQUENCE: 1

```
tatagaatcc aaaatgtata gaccctttat taactttctt agcaaaatat cttcagcacc      60
aatactagca tttagtatag aatccaaaat gtatagaccc ttgattaact ttattagcaa     120
aatatcttaa gtaccattat tagcaactag                                       150
```

<210> SEQ ID NO 2
<211> LENGTH: 75
<212> TYPE: DNA

<213> ORGANISM: Phalaenopsis bellina

<400> SEQUENCE: 2
tatagaatcc aaaatgtata gacccttgat taactttatt agcaaaatat cttaagtacc    60
attattagca actag    75

<210> SEQ ID NO 3
<211> LENGTH: 29
<212> TYPE: DNA
<213> ORGANISM: Artificial Sequence
<220> FEATURE:
<223> OTHER INFORMATION: forward primer for dual repeat

<400> SEQUENCE: 3
ttgcctcgag atttgtttcg gaggatgga    29

<210> SEQ ID NO 4
<211> LENGTH: 26
<212> TYPE: DNA
<213> ORGANISM: Artificial Sequence
<220> FEATURE:
<223> OTHER INFORMATION: reverse primer for dual repeat

<400> SEQUENCE: 4
acctaaggat gcatgggcca tactag    26

<210> SEQ ID NO 5
<211> LENGTH: 35
<212> TYPE: DNA
<213> ORGANISM: Artificial Sequence
<220> FEATURE:
<223> OTHER INFORMATION: forward primer for GDPS gene

<400> SEQUENCE: 5
atggcagcaa tctttccctc aatcccctcc aattt    35

<210> SEQ ID NO 6
<211> LENGTH: 19
<212> TYPE: DNA
<213> ORGANISM: Artificial Sequence
<220> FEATURE:
<223> OTHER INFORMATION: reverse primer for PDGS gene

<400> SEQUENCE: 6
cgaggggagg ggcggtgcg    19

<210> SEQ ID NO 7
<211> LENGTH: 19
<212> TYPE: DNA
<213> ORGANISM: Artificial Sequence
<220> FEATURE:
<223> OTHER INFORMATION: forward primer for promoter

<400> SEQUENCE: 7
gcctcgagat ttgtttcgg    19

<210> SEQ ID NO 8
<211> LENGTH: 29
<212> TYPE: DNA
<213> ORGANISM: Artificial Sequence
<220> FEATURE:
<223> OTHER INFORMATION: reverse primer for promoter

<400> SEQUENCE: 8
ccatggtttt tttgggtttg aaaggagag    29

<210> SEQ ID NO 9
<211> LENGTH: 32
<212> TYPE: DNA
<213> ORGANISM: Artificial Sequence
<220> FEATURE:
<223> OTHER INFORMATION: forward primer for PbGp-859

<400> SEQUENCE: 9
ggatcctata gaatccaaaa tgtatagacc ct                          32

<210> SEQ ID NO 10
<211> LENGTH: 29
<212> TYPE: DNA
<213> ORGANISM: Artificial Sequence
<220> FEATURE:
<223> OTHER INFORMATION: reverse primer for PbGp-859

<400> SEQUENCE: 10
ccatggtttt tttgggtttg aaaggagag                              29

<210> SEQ ID NO 11
<211> LENGTH: 30
<212> TYPE: DNA
<213> ORGANISM: Artificial Sequence
<220> FEATURE:
<223> OTHER INFORMATION: forward primer for PbGp-784

<400> SEQUENCE: 11
ggatccgaat ccaaaatgta tagacccttg                             30

<210> SEQ ID NO 12
<211> LENGTH: 29
<212> TYPE: DNA
<213> ORGANISM: Artificial Sequence
<220> FEATURE:
<223> OTHER INFORMATION: reverse primer for PbGp-784

<400> SEQUENCE: 12
ccatggtttt tttgggtttg aaaggagag                              29

<210> SEQ ID NO 13
<211> LENGTH: 31
<212> TYPE: DNA
<213> ORGANISM: Artificial Sequence
<220> FEATURE:
<223> OTHER INFORMATION: forward primer for PbGp-710

<400> SEQUENCE: 13
ggatccgccc atgcatcctt aggtctgtta a                           31

<210> SEQ ID NO 14
<211> LENGTH: 29
<212> TYPE: DNA
<213> ORGANISM: Artificial Sequence
<220> FEATURE:
<223> OTHER INFORMATION: reverse primer for PbGp-710

<400> SEQUENCE: 14
ccatggtttt tttgggtttg aaaggagag                              29